United States Patent
Castaneda

(10) Patent No.: US 7,282,177 B2
(45) Date of Patent: Oct. 16, 2007

(54) STETHOSCOPE CLEANSING UNIT AND BUSINESS METHOD FOR PROVIDING ADVERTISING THROUGH THE USE OF STETHOSCOPE CLEANSING UNIT

(76) Inventor: C. Robert Castaneda, 18706 Redriver Trail, San Antonio, TX (US) 78259

( * ) Notice: Subject to any disclaimer, the term of this patent is extended or adjusted under 35 U.S.C. 154(b) by 420 days.

(21) Appl. No.: 10/810,346

(22) Filed: Mar. 26, 2004

(65) Prior Publication Data

US 2005/0214185 A1    Sep. 29, 2005

(51) Int. Cl.
*A61L 1/00* (2006.01)
(52) U.S. Cl. .................. 422/28; 422/292; 422/300; 283/56
(58) Field of Classification Search .............. 422/28, 422/292, 300; 283/56; D20/10, 19
See application file for complete search history.

(56) References Cited

U.S. PATENT DOCUMENTS 3,530,261 A * 9/1970 Raul ........................ 379/452

2004/0258560 A1* 12/2004 Lake et al. .................. 422/28

* cited by examiner

*Primary Examiner*—John Kim
*Assistant Examiner*—Sean E. Conley
(74) *Attorney, Agent, or Firm*—David Henry

(57) ABSTRACT

The invention is of a stethoscope cleansing unit and of the use of the stethoscope cleansing unit as a novel business method for promoting a marketer's logo and advertisement to medical personnel and patients in the examining room or hospital. The system attaches such advertisements to a useful and conveniently used stethoscope cleansing unit that will be used by medical personnel to sterilize stethoscope diaphragms between patient assessments, thereby preventing the spread of infectious diseases. This apparatus can be utilized in a novel business method as a way for marketers to distinguish their product from the myriad of others by 1) attracting the attention of busy medical personnel during patient examinations, which is the exact time that medical product marketers would benefit most from such attention; and by 2) attracting the attention of the patient through its presence in the examining room at a time when the patient is typically waiting for attention and has time to notice such advertisements.

2 Claims, 1 Drawing Sheet

STETHOSCOPE CLEANSING UNIT AND BUSINESS METHOD FOR PROVIDING ADVERTISING THROUGH THE USE OF STETHOSCOPE CLEANSING UNIT

BACKGROUND OF THE INVENTION

1. Field of the Invention

The present invention relates to the field of medical instrument care and business methods in medical advertising and sales.

2. Background Information

We have a near epidemic of hospital-borne opportunistic infections that are transmitted primarily to the very young, the very old, and the very weak. These three populations are in the majority in every hospital population around the country. What can be done to prevent the spread of these infections? Proper aseptic technique, simple procedures such as frequent hand-washing, and proper cleansing of medical equipment can all be used to help prevent the spread of infections such as Nosocomial Pneumonia, one common bacterial infection that is spread in hospitals. Such drastic measures as "single use medical devices" have been proposed to help solve this problem. The solution we propose today is much cheaper, much simpler, and much more practical.

The stethoscope is a piece of medical equipment that no doctor can be without. The typical doctor uses a stethoscope dozens of times a day. And yet, less than 2% of the estimated 30 million stethoscopes in use today are cleaned between patient assessments. That part of the stethoscope that comes in contact with the patient is called the diaphragm and it can harbor untold numbers of germs. If doctors and nurses were given a simple, quick, convenient way to sterilize their stethoscope diaphragms they would be much more likely to perform this simple, yet effective task. Currently, they must hunt down a bottle of alcohol and a cotton ball, saturate the cotton ball with alcohol, and then disinfect their stethoscope diaphragm. Or, they must find an individual alcohol packet, tear it open, sterilize their stethoscope, and then discard the trash.

With today's invention it takes one second and a quick swipe to sterilize the one piece of medical equipment that virtually every patient comes in contact with—the stethoscope. By quickly inserting the stethoscope diaphragm into the stethoscope cleansing unit and then removing, medical personnel can ensure a clean, sterile surface with which to examine their next patient.

One of the main challenges in advertising to the medical community is providing advertising that will actually make an impression on a busy doctor or nurse. Combine a method that will make an impression with a method that will actually be of great use to members of the medical community and their patients, and you would have an unbeatable combination. The present invention is just such a method.

The method of advertising proposed by the present business method takes the common practice of "give-aways" to a new and practical height. Typically, doctors and nurses are given pencils, pads, combs, fingernail files, key holders, demonstration tools, or any number of small gifts that are emblazoned with a marketer's logo and are meant to keep the advertising company's name in mind. These items end up at home, in the car, with the spouse or children, stuck in a drawer, or in the trash. With today's advertising method, the proposed give-away is something useful, practical, and is meant to be kept in every examining room, right beside the ever-present box of disposable gloves. These give-aways are stethoscope cleansing units that are compact and effective. In only one second, the doctor or nurse can disinfect her stethoscope diaphragm and move on to the next patient. All the while being subtly influenced by the message on the stethoscope cleansing unit itself.

Further, while its presence in the examining room makes the stethoscope cleansing unit convenient for medical personnel to use, and therefore an ideal location for medical products advertising, the fact that the patient is typically kept waiting in examining rooms makes all objects found in that room "prime real estate" for any marketer's advertisement. Who hasn't spent many minutes, or even hours, waiting in an examining room for the doctor? The time is usually spent gazing about the room looking for something interesting to see or read. That is exactly why medical examining rooms always have public service posters in them. Where else can be found such a captive audience for a poster on the heartbreak of fungal toe infections? The presence of any retail marketer's advertisement on a stethoscope cleansing unit, placed conveniently beside the disposable gloves, will be seen and read by virtually all patients who find themselves waiting in that examining room. This novel business method of advertising has a captive, and therefore attentive, audience.

SUMMARY OF THE INVENTION

In view of the foregoing, it is an object of the present invention to provide a useful apparatus for preventing the spread of disease in a medical setting.

It is another object of the present invention to benefit medical personnel and patients by giving the medical personnel an easy, fast, convenient way to sterilize stethoscope diaphragms between patient assessments.

It is a further object of the present invention to have a stethoscope cleansing unit available in each examining room with the medical personnel and patient so that medical personnel will be reminded and motivated to cleanse their stethoscopes between patient assessments.

In view of the foregoing, it is another object of the present invention to provide a novel business method which benefits retail marketers, medical personnel, and patients.

It is another object of the present invention to provide a novel business method for promoting and selling many different types of medical products to the medical community. Also, it is an object of the present invention to provide a novel business method for promoting and selling many different types of products to medical patients.

It is a further object of the present invention to provide a novel business method for promoting and selling many different types of products to the medical community and patients by providing an easy, quick way for medical personnel to sterilize their stethoscope diaphragms, while at the same time advertising a marketer's logo right inside the examining room.

In satisfaction of these and other related objectives, Applicant's present invention provides for a way to advertise to medical personnel and patients, inside the hospital or examining room, while also providing a highly practical, effective, and useful way to help prevent the spread of infectious diseases among personnel and patients. The use of small, easily used, stethoscope cleansing units to advertise medical products and services will enable the marketer to keep his logo in front of medical personnel at a time in which the use of such products and services would most be at issue: during patient examinations. In addition, the use of these small, easily used stethoscope cleansing units to advertise other retail products and services will enable the marketer to keep his logo in front of patients at a time in which they would be most likely to have the time to read such advertisements: during lengthy waiting periods in the exam room.

Applicant's approach to the problem described above is certainly simple, but it is equally unobvious. Applicant's apparatus and novel business method facilitate for the first time absolution to the problem of how to quickly and easily sterilize a stethoscope diaphragm, while at the same time keeping a marketer's logo in front of potential costumers at the precise time that they would be most likely to appreciate the marketer's goods or services, thereby encouraging them to choose marketer's product.

DETAILED DESCRIPTION OF THE PREFERRED EMBODIMENT

Figure 1:
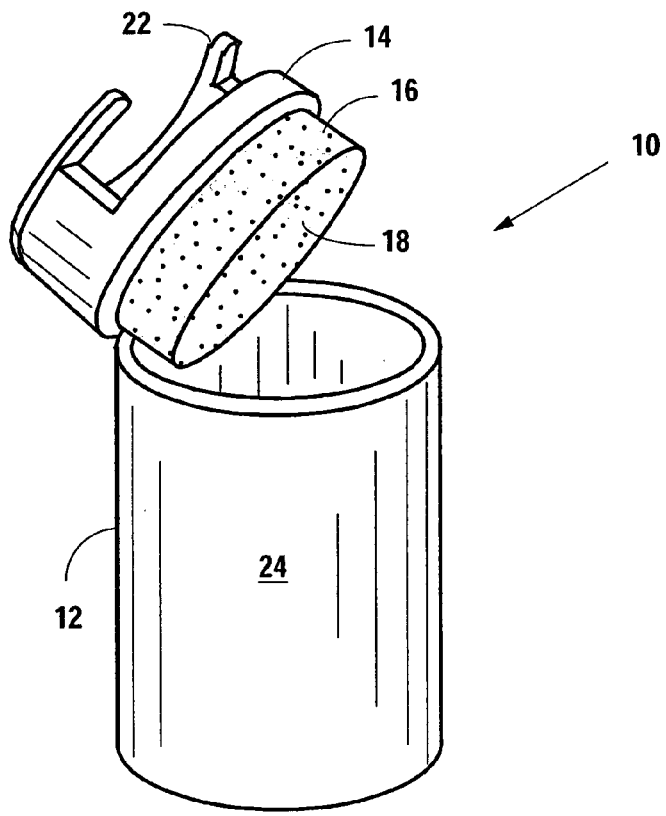
FIG. 1 is a perspective view of a stethoscope cleansing unit of the present invention with its lid member open
Figure 2:
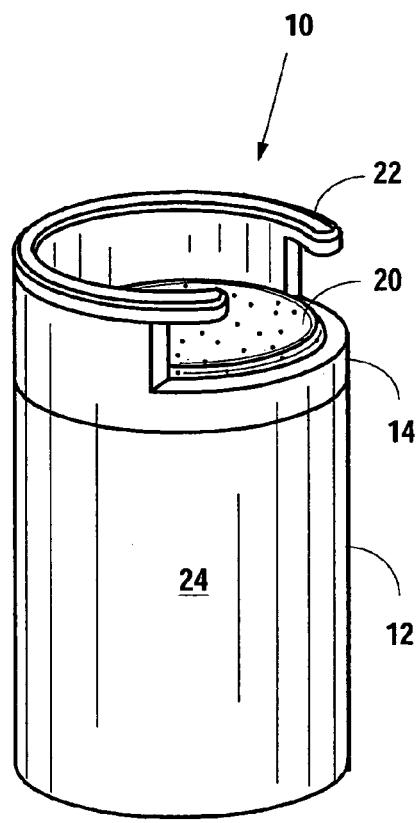
FIG. 2 is a perspective view of a stethoscope cleansing unit of the present invention with its lid member shut.

With reference to FIGS. 1 and 2, the stethoscope cleansing unit of the present invention is identified generally by the reference number 10.

Cleansing unit 10 includes a holding chamber 12, which in the preferred embodiment would hold 2–3 ounces of isopropyl alcohol, or other antiseptic liquid (not shown in the figures) such as is commonly known in the medical field. Chamber lid member 14 can open and close on hinges such as are conventionally used (not shown in figures) or can simply fit snugly on top of holding chamber 12. Wicking member 16 would be a sponge in the preferred embodiment, but could be some other similar absorbant material. Distal end 18 absorbs the antiseptic liquid found in holding chamber 12 and this end would most likely reach to the bottom of holding chamber 12 (not shown in figures).

In the preferred embodiment, the doctor or nurse would slip his stethoscope (not shown) under the stethoscope-receiving member 22, making contact between the diaphragm of the stethoscope and proximal end 20 of the wicking member 16. This allows the diaphragm (not shown in the figures) to come into contact with the antiseptic liquid found in holding chamber 12, which has wicked up wicking member 16.

One aspect of the present invention is its use in promoting retail product selection. In this novel business method, businesses that market to the medical community, or other businesses, would have their logo or other advertisement embossed, or otherwise attached to the outside surface 24 of holding chamber 12. Various designs, colors, or patterns could be used to further enhance the appearance of the stethoscope cleansing unit. Medical practitioners would be encouraged to position the stethoscope cleansing unit in the examining room, right beside the disposable examining gloves, making usage convenient and exposure of medical personnel and patients to the advertisement constant.

Although the invention has been described with reference to specific embodiments, this description is not meant to be construed in a limited sense. Various modifications of the disclosed embodiments, as well as alternative embodiments of the inventions will become apparent to persons skilled in the art upon reference to the description of the invention. It is, therefore, contemplated that the appended claims will cover such modifications that fall within the scope of the invention.

I claim:

1. A stethoscope cleansing unit, said lid member having:
    a holding chamber with reversibly opening chamber lid member, said holding chamber with an inner core comprising a wicking member extending distally down through said holding chamber and proximally up through an opening in said reversibly opening chamber lid member;
    a measure of antiseptic liquid inside said holding chamber and suitable for wicking by said wicking member; and
    a stethoscope-receiving member attached to said chamber lid member, allowing access to proximal end of said wicking member.

2. A business method for advertising medical products or services to medical personnel comprising the steps of:
    selecting a stethoscope cleansing unit comprising:
        a holding chamber with reversibly opening chamber lid member, said holding chamber with an inner core, said lid member having a wicking member extending distally down through said holding chamber and proximally up through an opening in said reversibly opening chamber lid member;
        a measure of antiseptic liquid inside said holding chamber and suitable for wicking by said wicking member; and
        a stethoscope-receiving member attached to said chamber lid member, allowing access to proximal end of said wicking member;
    attaching individual marketer's logo or other advertising to said stethoscope cleansing unit; and
    positioning for viewing by patients and medical personnel said stethoscope cleansing units in medical service facilities.

* * * * *